United States Patent [19]

Kummer

[11] Patent Number: 5,062,433
[45] Date of Patent: Nov. 5, 1991

[54] PROTECTOR PAD

[75] Inventor: Frederick J. Kummer, Brooklyn, N.Y.

[73] Assignee: Hospital for Joint Diseases, New York, N.Y.

[21] Appl. No.: 465,387

[22] Filed: Jan. 16, 1990

Related U.S. Application Data

[63] Continuation of Ser. No. 319,613, Mar. 6, 1989, abandoned.

[51] Int. Cl.[5] ............................................. A61F 13/00
[52] U.S. Cl. ..................................... 128/888; 128/846
[58] Field of Search ............... 128/846, 877, 882, 888, 128/156, 165

[56] References Cited

U.S. PATENT DOCUMENTS

| | | | |
|---|---|---|---|
| 729,293 | 5/1903 | Dorman | 128/888 |
| 3,026,874 | 3/1962 | Stevens | 604/305 |
| 3,304,938 | 2/1967 | Perkins, Jr. | 128/888 |
| 3,334,626 | 8/1967 | Schimmel | 128/888 |
| 3,528,416 | 9/1970 | Chamberlain | 128/888 |
| 4,023,569 | 5/1977 | Warnecke et al. | 128/888 |
| 4,250,882 | 2/1981 | Adair | 604/355 |
| 4,399,816 | 8/1983 | Spangler | 128/888 |
| 4,641,641 | 2/1987 | Strock | 128/846 |
| 4,905,681 | 3/1990 | Glascock | 128/888 X |
| 4,917,112 | 4/1990 | Kalt | 128/888 X |
| 4,926,883 | 5/1990 | Strock | 128/888 |

Primary Examiner—Robert A. Hafer
Assistant Examiner—Kevin G. Rooney
Attorney, Agent, or Firm—Stephen E. Feldman

[57] ABSTRACT

A protector to prevent hip fracture and/or bed-sores and/or protect a wound or wound area is formed from an outer load bearing member reinforced by internal ridges. The protector is dome shaped with structured ridges to form an internal dome or clearance for the region of desired protection. A soft inner sheet is attached for comfort. This structure has less bulk and weight than a solid pad. The outer shell formation distributes the load or pressure to the edges of the device, protecting the organ covered by the dome. The pad may have different internal ridge patterns to provide flexibility for user comfort.

11 Claims, 2 Drawing Sheets

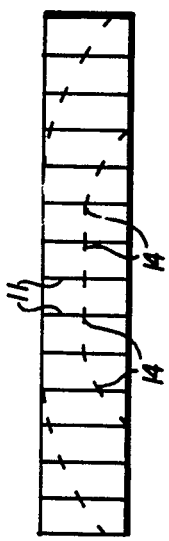
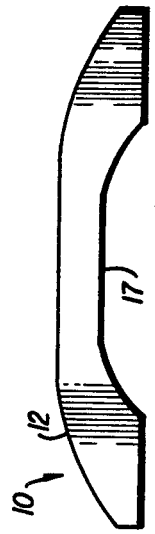
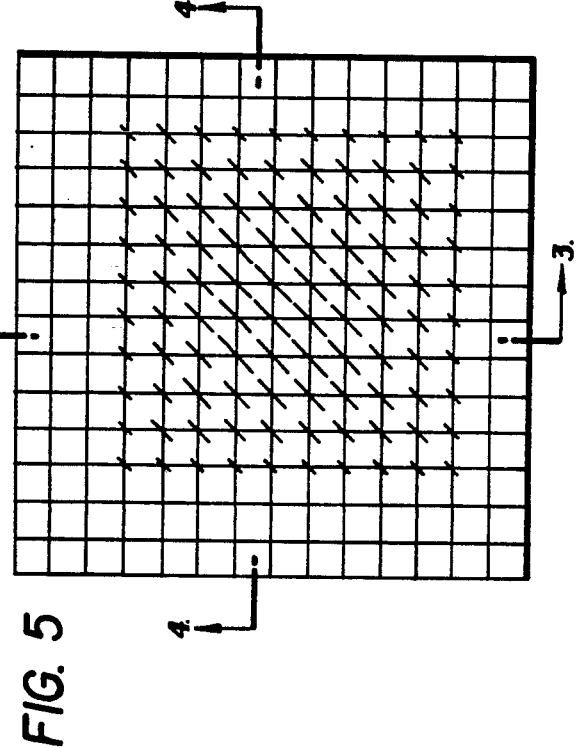
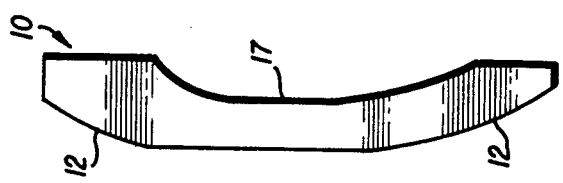
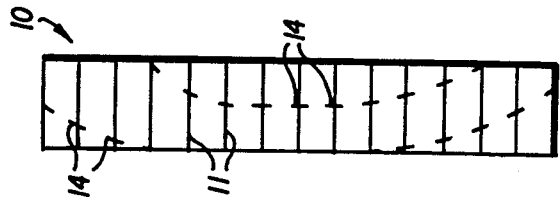
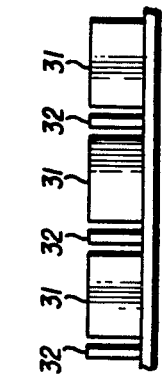
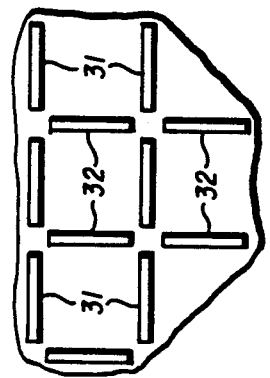

PROTECTOR PAD

This application is a continuation of Ser. No. 319,613 filed on Mar. 6, 1989, now abandoned.

BACKGROUND OF THE INVENTION

1. Field of the Invention

The present invention relates to pads or padded bandages particularly useful in covering and/or protecting the body from injury and/or covering and/or protecting an injury or wound on the body. In particular the present invention is a light-in-weight and reduced-in-bulk pad useful particularly in the upper leg and hip area for preventing injury to the hip. It can also prevent sores from occurring and be used for protecting the upper leg and hip region where the individual using the padded bandage has been subjected to surgery on the hip or some wound in the upper leg and/or hip region.

2. Prior Art

There are, in the United States alone, approximately 150,000 to 200,000 hip fractures each year. Many of the hip fractures require surgical procedures to properly align the fractured bone so as to promote proper healing. Surgery, especially hip surgery, normally results in a wound on the outside of the hip region, which is more often difficult to protect, especially when the patient becomes ambulatory. Protective pads have been designed to protect hip surgical wounds and other hip wound areas. Some of these are large domelike pads formed by a large, rigid outer shell. The size of the wound and/or wound area dictates the size of the protective pad to be used and as the size of the wound and/or wound area increases both the bulk and weight of the protective pad increase.

The overall bulk of this type of hip region protective pad is objectionable, to the user of such pad, especially since the rigid shell forming it is not flexible.

SUMMARY OF THE INVENTION

The present invention overcomes the objections directed at the rigid large bulk, and by heavy shell type protective pad.

Particularly, the present invention is a multi-component protective pad having an inner soft pad, an outer load bearing cover support, and an inner support of geometrically shaped cells, formed by internal ridges, which serve as a base for the pad. The inner soft pad or sheet may be a relatively thin foam sheet material that makes contact with the bandage or skin. The outer load bearing cover serves to transmit any load or pressure to the inner support which distributes such load or pressure to the edge regions of the inner support. The outer load bearing cover may also serve as a moisture barrier for the pad.

The ridges may be in the form of a block of simple shaped geometric cells with open ends. The preferred shape being square in construction with essentially geometric shaped chambers with interrupted interstices. The mass of cells forms a protective shield over the region to be protected. The walls of the cells form a protection shield or comb that protects the wound or wound-area or swelling to be covered, giving both space and air to the wound area without a bulky dome. The network of cells provides a strong rigid foundation for the pad. The bulk is avoided because the construction is inherently open but strong.

The foam sheeting may be cut to contour the formed mass of cells, and the moisture barrier forming the exterior of the pad may be cut and/or perforated so as to provide the moisture guard and permit air circulation.

Air circulation is inherent in a pad so made because of the openness of the cells forming the center mass of the pad.

When the center mass or block of cells is made from an injection plastic, the walls may be made thick enough for the required strength needed for a pad but thin enough to permit sculpturing the inside of the mass of cells to provide the dome effect or clearance required over the wound area.

BRIEF DESCRIPTION OF THE DRAWINGS

FIG. 3a is a side view through line 3—3 of FIG. 5 of the unshaped cell mass in cross section;

FIG. 3b is a side view, through line 3—3 of FIG. 5 of the shaped cell mass in cross section;

FIG. 4a is a top view through line 4—4 of FIG. 5 of the unshaped cell mass in cross section;

FIG. 4b is a top view, through line 4—4 of FIG. 5 of the shaped cell mass in cross section;

FIG. 5 is a representation of a block of cells with the perimeter formed and the interior scooped out as shown in broken line form.

FIGS. 6a and 6b represent in plan view and side elevation an alternate structure of the block of cells.

DETAILED DESCRIPTION OF THE DRAWINGS

Figure 1:
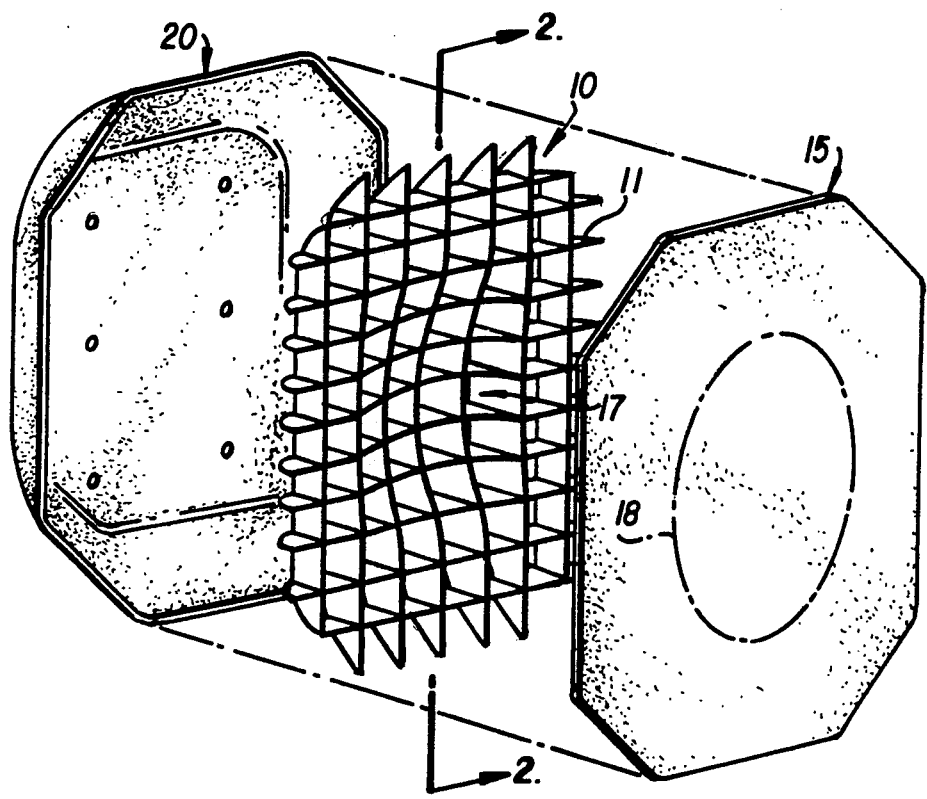
FIG. 1 is a representation of the invention with the parts exploded.

Referring to the drawings in general, the various components and/or part of the invention are similarly numbered or labeled throughout the various Figs.

Figure 1A:
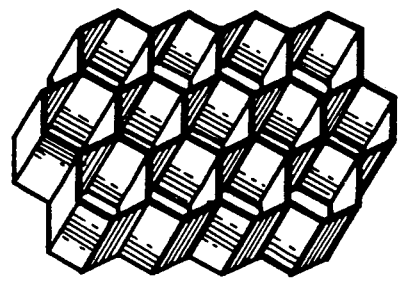
FIG. 1a is a representation of an alternate cell geometry.

FIG. 1 shows the invention in exploded view. Preferably the pad is a three element pad, although the pad may have more or fewer elements. The central and most basic component is a mass or block of cells 10 that is illustrated in perspective view. As shown in FIG. 1, the cells are rectangular in form, preferably square, because of simplicity of manufacture. The cells could be any reasonable shape, such as honeycomb, for example, shown in FIG. 1a so long as it forms a block or mass of cells, the walls of which have a depth. The block of cells may be made of any lightweight, formable material, plastic being the preferred material but not the only material. Various other materials, such as paper, cardboard, foam or other light weight material that may be cut, may be used.

As illustrated, the walls 11, have a thickness, and in the unsculptered form, such as represented in FIG. 5, the mass or block of cells may be in the form of a rectangular block or mass.

The outer sheet 20 is represented as having holes 22 which encourage air flow through the pad.

Figure 2:
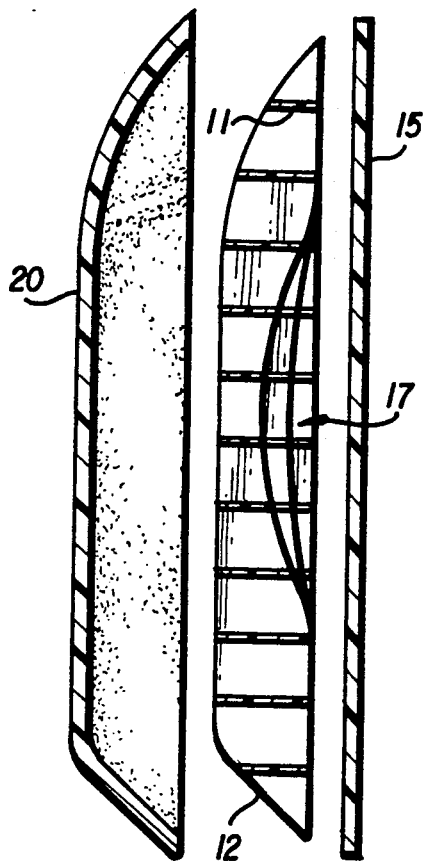
FIG. 2 is a cross section view of the invention, the section taken through line 2—2 of FIG. 1.

FIG. 2 represents in a side elevation, a cross sectional view of the pad along the line 2—2 in FIG. 1. It will be noted that the ridge is shaped at 17, by reducing the depth of the cell walls from the inside, or may be shaped from the outside as at 12 by reducing the depth of the cell walls from the outside. Reduction in the depth of the walls may be made by initially casting or vacuum forming or cutting, grinding or chipping away the walls where desired to contour the block of cells.

In FIGS. 3a and 4a the unsculptered block 10 is represented with broken lines 14. The broken lines 14 represent where the walls of the cells may be cut or ground away so as to contour or shape them such as represented in FIGS. 3b and 4b respectively.

FIG. 5 shows in plan view a structure in which the cells are square. As stated previously, the cells could be other geometric shape. The broken line 14 shows where the wall of the cells may be cut or sculptured so as to shape the pad as desired.

It will be apparent that the pad may be secured to the body of the patient. The pad itself may also be incorporated into a tie, or incontinent device if desired.

The present invention has great utility in protecting a hip wound or hip wound area since the overall pad is relatively thin. In addition the sculptured interior of the block of cells gives wound or wound area clearance, and provides protection for the wound or wound area and the surrounding area. This is done without bulk or weight because of the inherent strength of the cell structure and the light weight of the material from which a block of cells may be made.

The size of the outer shell used depends on the size of the wound or wound area desired to be covered. The size and shape of the interior clearance of the pad may be as desired, as demanded by the body area to be covered.

FIGS. 6a and 6b represent the preferred structure of cell block where the walls forming the cells are in the form of raised ribs 31 and cross ribs 32 on a base 33.

Thus there has been described and shown a preferred embodiment of the invention and several alternate structures have been suggested. Other changes and modifications may be made, as will be apparent to those skilled in the art after reading the above disclosure, without departing from the spirit of the invention as defined in the claims.

What is claimed is:

1. A protector pad for protecting a hip or other area on the body, said protector pad comprising:
   (a) a plurality of walls defining a plurality of substantially uniformly shaped rigid cells, said plurality of walls having a length and a width and a thickness, said thickness defining the depth of the cells of said plurality of cells;
   (b) said length and said width of said plurality of walls at least exceeding the length and width of a wound or a wound area to be protected by said protector pad; and
   (c) wherein the walls defining selected adjacent cells are progressively reduced in said thickness for forming a concave section in said plurality of walls for providing a clearance over said wound or wound area.

2. A protector pad as in claim 1 and further including a soft resilient barrier sheet between said plurality of walls adjacent said concave section and said would or said wound area.

3. A protector pad as in claim 1 and in which said plurality of walls are ribs and cross rib elements extending from a base and defining the cells of said plurality of cells and said plurality of cells are open at least at one end.

4. A protector pad for covering and protecting a wound area on a body, said protector pad comprising:
   a) an outer protective sheet defining an outer cover of said protector pad;
   b) an inner soft resilient sheet for providing soft, resilient contact with said protector pad; and,
   c) a plurality of cells sandwiched between said outer protective sheet and said inner soft resilient sheet, said plurality of cells defined by a plurality of walls aligned in a geometric pattern defining uniform geometric shaped cells, adjacent walls, of said plurality of walls, of selected cells being progressively reduced in depth adjacent said inner soft resilient sheet for providing a clearance in said plurality of cells, over said wound area.

5. A protective pad as in claim 4 and in which said cells defined by said walls are rectangular.

6. A protective pad as in claim 4 and in which said cells defined by said walls are hexagonal.

7. A protective pad as in claim 4 and in which said cells defined by said walls are curved.

8. A protective pad as in claim 4 and in which said cells are formed by a plurality of ribs and cross ribs standing on a base.

9. A protector pad as in claim 4 and in which said plurality of walls are a plurality of ribs and cross rib elements, standing on a base.

10. A protector pad as in claim 4 and in which said plurality of walls are a plurality of internal ridges standing on a base and said internal ridges are aligned forming a geometric shape.

11. A protector pad for covering and protecting a wound or wound area on a body, said protector pad comprising:
   (a) an outer protection sheet defining an outer cover of said protector pad;
   (b) an inner soft resilient sheet for providing soft, resilient contact with said protector pad; and,
   (c) a plurality of cells formed by a plurality of walls, each cell of said plurality of cells being substantially similar in shape, relative to adjacent cells, said plurality of cells disposed between said outer protection sheet and said inner soft resilient sheet, each wall of said plurality of walls having a depth, said walls defining substantially similarly shaped cells and said depth of said walls defining a thickness of said plurality of cells, said walls of selected adjacent cells being progressively reduced in depth adjacent said inner soft resilient sheet for providing a concave shaped clearance in said plurality of cells over said wound or wound area.

* * * * *